United States Patent [19]

Didion et al.

[11] Patent Number: 5,714,642
[45] Date of Patent: Feb. 3, 1998

[54] RESOLUTION OF IMMIXTURES OF STEREOISOMERIC ALCOHOLS

[75] Inventors: Christophe Didion, Epinal; Dominique Petre, Lyons, both of France

[73] Assignee: Rhone-Poulenc Chimie, Courbevoie Cedex, France

[21] Appl. No.: 523,469

[22] Filed: Sep. 5, 1995

[30] Foreign Application Priority Data

Sep. 5, 1994 [FR] France .................................. 94 10604

[51] Int. Cl.$^6$ .................................................. C07C 29/74
[52] U.S. Cl. .......................... 568/810; 568/817; 568/829; 568/834
[58] Field of Search ..................... 568/810, 834, 568/817, 829

[56] References Cited

FOREIGN PATENT DOCUMENTS 407033  1/1991  European Pat. Off. .
605033  7/1994  European Pat. Off. .

OTHER PUBLICATIONS

Biotechnol. Bioeng., 1984, 26(12), 1449–54 Coden:Bibiau;ISSN:0006-3592.
J.Am.Chem.Soc. (1984), 106(9), 2687–92 Coden:Jacsat;ISSN:0002-7863.
Methods Enzymol.(1987), 136(Immobilized Enzymes Cells, PT.C), 117–37 Coden:Menzau;ISSN:0076-6879.
J.Am.Chem.Soc. (1987), 109(9), 2812–17 Coden:Jacsat;ISSN:0002-7863.
Chemical Abstracts, vol. 113, No. 13, Sep. 24, 1990, Columbus, Ohio, abs. No. 113833.
Biotechnol Bioeng 41 (1). 1993. 95–103. Coden:Bibiau ISSN: 0006-3592.
J.Am Oil Chem Soc 69 (4), 1992, 295–300.
Biological Abstracts, vol. BA93, Phila, PA, abs. No. 39728, 1992.
Chemical Abstracts, vol. 116, No. 25, Jun. 22, 1992, Columbus, Ohio, abs. No. 250944.
Chemical Abstracts, vol. 111, No. 23, Dec. 4, 1989, Columbus, Ohio, abs. No. 213302.

Primary Examiner—Samuel Barts
Attorney, Agent, or Firm—Burns, Doane, Swecker & Mathis, L.L.P.

[57] ABSTRACT

Immixture of stereoisomeric alcohols is resolved by selectively enzymatically acylating one of the stereoisomers thereof, in the presence of a catalytically effective amount of a hydrolase, for example a lipase, esterase or acylase, in a biphasic hydroorganic reaction medium, and thence separating the alcohol stereoisomer from the ester stereoisomer thus formed.

31 Claims, No Drawings

RESOLUTION OF IMMIXTURES OF STEREOISOMERIC ALCOHOLS

BACKGROUND OF THE INVENTION

1. Technical Field of the Invention

The present invention relates to the resolution of immixtures of stereoisomeric alcohols, and, more especially, to the enzymatic separation of one of the two stereoisomers by selective acylation.

2. Description of the Prior Art

Production of pure optically active compounds presents a problem which is encountered in a variety of technical fields such as pharmacy, agrochemistry, the food industry (food additives, flavorants) and in the perfume industry, etc.

This problem can be expected to increase in importance, since, more and more often, it is demonstrated that, for a given application, only one of the stereoisomers exhibits the desired properties.

To overcome this problem, a number of techniques have been proposed which entail resolution via enzymatic catalysis.

Thus, Faber et al describe a process for the separation of chiral alcohols in an organic medium [Synthesis, pp 895 ff (1992)].

However, the majority of the known processes are difficult to extrapolate to an industrial scale.

Thus, serious need exists for an industrial process which would essentially exclusively produce one desired stereoisomer.

SUMMARY OF THE INVENTION

Accordingly, a major object of the present invention is the provision of a novel process for the resolution of a mixture of stereoisomeric alcohols, comprising reacting said mixture with a selective acylation agent in the presence of a hydrolase, in a biphasic, hydroorganic reaction medium, and thence separating the esterified isomer from the nonesterified isomer to recover one of the stereoisomers of the alcohol and the ester of the other stereoisomer.

DETAILED DESCRIPTION OF BEST MODE AND PREFERRED EMBODIMENTS OF THE INVENTION

More particularly according to the present invention, one of the characterizing features thereof is that the transesterification is carried out in a heterogeneous, biphasic hydroorganic reaction medium.

Numerous advantages are thus obtained. The enzymatic activity is higher than in an organic reaction medium and the reaction times are compatible with those required for industrial scale operation. In addition, at the end of the reaction, the alcohol and the ester obtained are in the organic phase and the enzyme is in the aqueous phase, which permits these species to be readily separated by simple separation of the phases. The aqueous phase, and thus the enzyme, can be recycled. In a preferred embodiment of the invention, the acylation or acylating agent is also in the aqueous phase.

The process of the invention is applicable to any mixture of stereoisomeric alcohols. The mixture is preferably primarily soluble in an organic medium and selection of the enzyme must take this into account.

A first category of substrates to which the invention is applicable is that of chiral alcohols, i.e., enantiomers comprising an asymmetric carbon atom.

In particular, these have the following formula (I):

$$R\text{---}OH \quad (I)$$

in which R is a hydrocarbon radical having at least 4 carbon atoms and which is monovalent, substituted or unsubstituted, and can be a linear or branched, saturated or unsaturated, acyclic aliphatic radical, or a monocyclic or polycyclic, saturated or unsaturated, carbocyclic or heterocyclic radical, with the proviso that the hydroxy group either may or may not be borne by the asymmetric carbon atom.

Preferably, R is the residue of a linear or branched, saturated or unsaturated aliphatic chiral alcohol which may be substituted by a cyclic ring member, or of a saturated or unsaturated, monocyclic, carbocyclic or heterocyclic chiral alcohol, or of a polycyclic, carbocyclic or heterocyclic chiral alcohol containing at least two saturated and/or unsaturated carbocycles.

The chiral alcohol employed in the process of the invention is more particularly one of formula (I) in which R is a linear or branched, saturated or unsaturated, acyclic aliphatic radical.

Preferably, R is a linear or branched alkyl, alkenyl, alkadienyl or alkynyl radical, preferably having from 4 to 40 carbon atoms.

The hydrocarbon chain or backbone of the radical R may be interrupted by a heteroatom (oxygen or sulfur, for example), or by one of the following groups:

$$\text{---CO---}, \text{---COO---}, \text{---OCOO---}, \text{---SO}_2\text{---}, \text{---}\underset{\underset{R_1}{|}}{N}\text{---},$$

$$\text{---CO---}\underset{\underset{R_1}{|}}{N}\text{---},$$

and/or bear one of the substituents ---OH, ---COOR$_1$, ---CHO, ---NO$_2$, ---X or CF$_3$, wherein R$_1$ is preferably hydrogen or a linear or branched alkyl radical having from 1 to 4 carbon atoms, preferably a methyl or ethyl radical.

The linear or branched, saturated or unsaturated, acyclic aliphatic radical may bear a cyclic substituent.

It can be bonded to the cyclic ring member by a simple valence bond or via one of the following groups:

$$\text{---O---}, \text{---CO---}, \text{---COO---}, \text{---OCOO---}, \text{---S---}, \text{---SO}_2\text{---},$$

$$\text{---}\underset{\underset{R_1}{|}}{N}\text{---}, \text{---CO---}\underset{\underset{R_1}{|}}{N}\text{---},$$

wherein R$_1$ is as defined above.

By the term "cycle" is intended a saturated, unsaturated or aromatic, heterocyclic or carbocyclic ring member.

Exemplary cyclic substituents include cycloaliphatic, aromatic or heterocyclic substituents, in particular cycloaliphatic substituents having 6 carbon atoms in the ring member, or benzenic substituents, these cyclic substituents optionally themselves being substituted by one or more substituents. Benzene nuclei are the preferred cyclic substituents.

Among the alcohols of formula (I), R is advantageously a monocyclic carbocyclic radical. The number of carbon atoms in the cyclic ring member can range from 3 to 8 carbon atoms, but is preferably 5 or 6 carbon atoms.

The carbocycle can be saturated or can contain one or two sites of unsaturation in the ring member, preferably 1 or 2 double bonds.

When R is a saturated or unsaturated, monocyclic carbocyclic radical, one or more carbon atoms of the cyclic ring member may be replaced by a heteroatom, preferably oxygen, nitrogen or sulfur, or by a functional group, preferably a carbonyl or ester group, thus defining a monocyclic heterocyclic compound. The number of atoms in the cyclic ring member can range from 3 to 8 carbon atoms, but is preferably equal to 5 or 6 atoms.

The radical R can also be polycyclic and carbocyclic, preferably bicyclic, i.e., comprising at least two ring members having two common carbon atoms. In the case of polycyclic radicals, the number of carbon atoms in each ring ranges from 3 to 6; the total number of carbon atoms is preferably 7.

The following are exemplary of the bicyclic ring members:

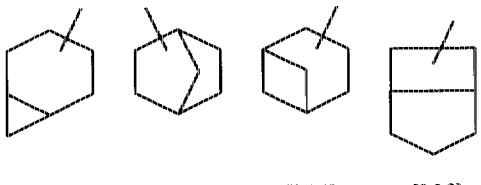

[4,1,0]   [2,2,1]   [3,1,1]   [3,2,0]

The radical R can also be polycyclic and heterocyclic, preferably bicyclic, connoting that at least two rings have two common carbon atoms. In this event, the number of atoms in each ring member ranges from 3 to 6, more preferably 5 or 6.

It should be appreciated that if radical R comprises a ring member, this cycle may bear a substituent. Any substituent is intended, provided that it does not interfere with the desired final product, i.e., is inert. The most typical substituents are one or more alkyl or alkoxy radicals preferably having from 1 to 4 carbon atoms, preferably three methyl radicals, a methylene radical (corresponding to an exocyclic bond), an alkenyl radical, preferably an isoprenyl radical, or a halogen atom, preferably chlorine or bromine.

The substrates which are preferably used in the process of the invention are linear or branched, saturated or unsaturated aliphatic alcohols having from 4 to 30 carbon atoms, which may be substituted, for example by a cyclic substituent, in particular a phenyl group, a halogen atom, an amine or an alkoxy group generally having 1 to 4 carbon atoms.

Particularly exemplary mixtures of stereoisomeric alcohols which are suited for the process of the invention include, among others, the mixture of stereoisomers of 2-phenyl-1-propanol (or hydratropic alcohol), 1-phenylethanol (or α-phenylethyl alcohol), menthol or nortricyclanol.

Another category of substrates which are well suited for the process of the invention are positional stereoisomers, in particular the stereoisomers of secondary cyclic alcohols, preferably cyclohexanol, one having the hydroxy group in the axial position and the other in the equatorial position. In these stereoisomers, conformation is blocked or sterically hindered by the presence of a bulky group, preferably an aliphatic or cycloaliphatic alkyl radical having at least 3 and up to 12 carbon atoms.

The following examples of alcohols illustrate this type of mixture of stereoisomers: 4-tert-butylcyclohexanol, 4-isobornylcyclohexanol and 4-isocamphylcyclohexanol.

It should be appreciated that the ratio between the two stereoisomers is immaterial. It can, for example, range from 0.3 to 1.0.

The acylation agent is preferably selected such as to be soluble in the aqueous phase.

Preferably, an organic acid ester or an organic acid anhydride is employed.

In particular, it preferably has the following formula (II):

(II)

wherein n is a number equal to 1, 2 or 3; $R_1$ is a lower alkyl radical; and if n=1, $R_2$ is a lower alkyl or alkenyl radical or a —CO—$R_3$ radical, in which $R_3$, which may be identical to or different from $R_1$, has the same definition as $R_1$, or if n=2, $R_2$ is a lower alkylene or alkenylene radical, or, if n=3, $R_2$ is a lower triyl alkyl radical.

By the expression "lower" is intended less than 4 carbon atoms, preferably less than 3 carbon atoms.

$R_1$ is preferably an alkyl radical having from 1 to 3 carbon atoms, such as methyl, ethyl, propyl or isopropyl, preferably a methyl radical.

When the acylation agent is an organic acid ester, the preferred compounds of formula (II) are those in which $R_2$ is a methyl or vinyl radical, a halogenomethyl radical, a mono-, di- or trihalogenomethyl radical, a methylsulfate radical, or an ethylsulfate radical, when n=1; a diethylene radical, when n=2; or a propan-1,2,3-triyl radical, when n=3.

When the acylation agent is an acid anhydride, the preferred compounds of formula (II) are those in which $R_1$ and $R_3$ are identical and represent an alkyl radical having from 1 to 3 carbon atoms.

The following are exemplary acylation agents:
Triacetin,
Vinyl acetate,
Acetic anhydride.

Triacetin is the preferred acylation agent for the process of the invention.

The transesterification reaction is carried out in the presence of a catalyst which is an enzyme selected from among the hydrolases, in particular lipases, esterases or acylases.

The enzymes are defined in the international nomenclature described in "Enzyme Nomenclature 1984, IUB, Academic Press Inc, (1984)".

In particular, a hydrolase is employed which belongs to class EC.3 using the above nomenclature (p 270), in particular carboxylesterases (3.1.1.1), triacylglycerol lipases (3.1.1.3) or acylases (3.5.1.4).

All of these types of enzyme are commercially available.

Exemplary enzymes which are well suited for the process of the invention are indicated below.

The lipases are derived from the organs (for example liver, panceas or saliva glands) of higher organisms such as cattle (calves), pigs, horses or rabbits, or are derived from microorganisms such as: *Geotricum candidum*, *Penicillium cyclopium*, *Penicillium roqueforti*, *Candida cylindracea*, *Rhizopus delemar*, *Rhizopus niveus*, *Mucor javanicus*, *Pseudomonas fluorescences*, and Pseudomonas species.

The esterases are, in particular, esterases from pig or horse liver and the acylases are obtained from microorganisms such as Aspergillus.

The preferred enzyme for use in the process of the invention is obtained from *Candida cylindracea*.

The enzymes can be free or supported.

The enzyme must be capable of discriminating one of the two stereoisomers in order to esterify the majority of only one stereoisomer.

In order to determine whether the enzyme is suitable for separation of the enantiomers, the enantiomeric ratio E must be measured and selected such that it is greater than 5, preferably greater than 10.

The enantiomeric ratio E is defined as:

$$E = \frac{\ln[1 - TT(1 + ee_p)]}{\ln[1 - TT(1 - ee_p)]}$$

wherein TT represents the transformation ratio of the substrate (one of the stereoisomers) and $ee_p$ represents the enantiomeric excess of the product obtained.

As indicated above, one of the features of the process of the invention is that the reaction is carried out in a biphasic medium comprising an aqueous phase and an organic phase constituted by at least one organic solvent which is not miscible with water.

The pH of the aqueous phase is selected such as to be compatible with the activity of the enzyme. In general, the pH ranges from 5 to 8, preferably from 5 to 7.

It may be necessary to add a neutralizing agent, usually caustic soda.

The amount added is sufficient to obtain the desired pH.

It is also possible to control the pH by adding a buffer such as a phosphate, carbonate, bicarbonate, borate, or an organic buffer such as tris(hydroxymethyl)amino methane.

An organic solvent which is not miscible with water is also employed.

A number of factors determine the selection of the solvent.

The solvent must dissolve all or a portion of the mixture of alcohols. It is preferable that the stereoisomers are completely dissolved.

A further condition is that the organic solvent is inert in respect of the transesterification reaction.

A preferred class of solvents comprises slightly polar, aprotic organic solvents.

Suitable solvents according to the process of the invention include:

(a) aliphatic hydrocarbons, in particular paraffins such as pentane, hexane, heptane, octane, isooctane, nonane, decane, undecane, tetradecane, petroleum ether and cyclohexane, aromatic hydrocarbons such as benzene, toluene, xylenes, ethylbenzene, diethylbenzenes, trimethylbenzenes, cumenes, pseudocumene, and petroleum cuts constituted by a mixture of alkylbenzenes, in particular Solvesso® type cuts;

(b) aliphatic or aromatic halogenated hydrocarbons, in particular perchlorinated hydrocarbons such as trichloromethane, carbon tetrachloride, tetrachloroethylene, hexachloroetehane, partially chlorinated hydrocarbons such as dichloromethane, dichloroethane, tetrachloroethane, trichloroethylene, 1-chlorobutane, and 1,2-dichlorobutane, and monochlorobenzene, 1,2-dichlorobenzene, 1,3-dichlorobenzene, 1,4-dichlorobenzene or mixtures of different chlorobenzenes; and (c) aliphatic, cycloaliphatic or aromatic ether/oxides, in particular diethylether, dipropylether, diisopropylether, dibutylether, methylteriobutylether, ditertiobutylether, the dimethylether of ethyleneglycol, the dimethylether of diethyleneglycol, diphenylether, dibenzylether, anisole, phenetole, 1,4-dimethoxybenzene, veratrol, 1,4-dioxane, and tetrahydrofuran (THF).

The preferred solvents are aliphatic and aromatic hydrocarbons, preferably pentane, heptane, petroleum ether, or toluene.

The amount of organic solvent employed varies widely. The volume ratio between the aqueous phase and the organic phase advantageously ranges from 0.1 to 10, preferably from 1.0 to 5.0. Preferred is a volume ratio of 1.0 or more.

The amount of water used is the amount of water necessary to be in excess of the solubility of the water in the organic solvent under consideration, with solubility being as defined in the literature. The amount of water preferably employed is in excess of this quantity, by at least 100%, and can be substantially greater.

The concentration of the mixture of stereoisomeric alcohols in the organic solvent is a function of its solubility. Advantageously, a high concentration is selected, on the order of 1 mole/liter.

The amount of acylation agent used, expressed with respect to the amount of alcohol stereoisomer to be transformed, is preferably at least equal to the stoichiometric amount. Preferably, it is introduced in a quantity greater than the stoichiometric amount. This excess can range from 1 to 40 with respect to the stoichiometry, preferably 1 to 5.

The amount of enzyme advantageously ranges from 0.1% to 100%, preferably 1% to 10% by weight with respect to the mixture of stereoisomeric alcohols.

The reaction temperature must be compatible with the activity of the enzyme. It is preferably less than 60° C., and more preferably ranges from 20° C. to 40° C.

The reaction is advantageously carried out at atmospheric pressure, but lower or higher pressures are also within the ambit of the invention.

From a practical standpoint, the process of the invention is simple to carry out.

A preferred embodiment of the present invention is given below.

First, the aqueous and organic phases are prepared separately.

The aqueous phase is constituted by a mixture of water, the enzyme and, optionally, an agent which provides the correct pH.

The mixture of stereoisomeric alcohols to be separated is introduced into the organic solvent which defines the organic phase.

The organic and aqueous phases are mixed and the reaction is initiated by adding the acylation agent to the mixture.

The reaction mixture is heated to the desired temperature, while stirring the reaction medium well.

The reaction time is a function of the transformation ratio of the alcohol to be esterified. When the enzyme selectivity is not high, a technique which is known to this art and which limits the transformation ratio, must be employed.

At the end of the reaction, the organic phase contains one of the stereoisomers in the esterified form, the other stereoisomer also remaining in that phase as the alcohol.

The organic and aqueous phases are separated.

The organic phase is treated to eliminate the organic solvent by distillation.

The ester obtained is separated from the alcohol using conventional separation techniques, preferably distillation or crystallization.

To obtain the other isomer, the ester can be retrograded to the alcohol via conventional techniques such as hydrolysis in an acidic medium (sulfuric acid, or trifluoromethanesulfonic acid).

The aqueous phase containing the enzyme is advantageously recycled.

It should be appreciated that it is also possible to acylate the stereoisomeric alcohol produced, and, in particular, via the acetylation thereof, employing conventional techniques described in the literature (Jerry March, *Advanced Organic Chemistry*, 4th Edition, p. 491, John Wiley and Sons (1992)), most notably acetylation by means of acetyl chloride or acetic anhydride.

The process of the invention is particularly well suited for the resolution of a variety of mixtures of stereoisomeric alcohols, in particular 4-tert-butylcyclohexanol, constituted by two stereoisomers distinguished by the presence of a hydroxy group in the axial or the equatorial position.

In a preferred embodiment, the mixture is transesterified with triacetin to separate the two stereoisomers according to the following reaction mechanism:

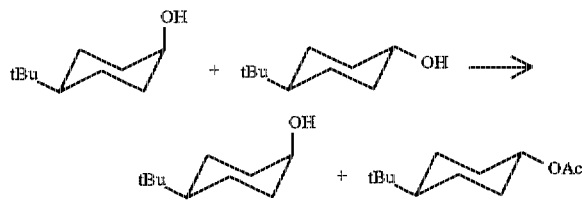

The process of the invention can thus be used to separate the isomer with the OH group in the axial position from the isomer with the OH group in the equatorial position.

The process according to the invention provides separate stereoisomeric alcohols or acylated alcohols, and, preferably, separate acetylated stereoisomeric alcohols.

These compounds are useful for a wide variety of applications, and, in particular, as pharmaceutical active agents/constituents.

Perfumes constitute another preferred application of the subject compounds.

Thus, they may be used as perfuming ingredients in perfuming compositions and perfumed substrates and products.

By the term "perfuming compositions" are intended mixtures of various ingredients, such as solvents, solid or liquid bases, fixing agents, various odoriferous compounds, etc., which incorporate the subject stereoisomeric alcohols or acylated stereoisomeric alcohols, these alcohols being formulated to impart the desired fragrance to various types of final products.

Perfume bases are preferred examples of perfuming compositions in which the compounds according to the invention are advantageously formulated.

Eaux de toilettes, after-shave lotions, perfumes, soaps, bath and shower gels, and deodorants and anti-perspirants, whether in stick or lotion form, are exemplary substrates or final products to which the compounds according to the invention impart a distinctive scent.

They may also be included in shampoos and hair-care products of all types.

Further, they can be used to perfume talcum powders and powders of all varieties.

Additionally, they may be incorporated into air deodorizers or any cleaning or maintenance product.

Conventional detergent compositions constitute another example of substrates in which the subject compounds may advantageously be formulated. These compositions generally include one or more of the following ingredients: anionic, cationic, or amphoteric surfactants, whitening agents, optical bleaching agents, various fillers, and anti-redeposition agents. The nature of these various constituents is not critical, and the compounds according to the invention may be included in any type of detergent composition. They may also be incorporated into textile softeners in liquid form or in compositions deposited onto substrates (typically nonwoven fabrics) for use in household dryers.

The compositions according to the invention contain proportions of the subject compounds, expressed as percentages by weight in the composition in question, and these percentages depend on the nature of the particular composition (e.g., base for perfume or eau de toilette) and on the power and character of the effect desired in the final product. It is apparent that, in a perfume base, the proportion of an optically active compound according to the invention may be very high, e.g., greater than 50% by weight, and may attain a value of 90% by weight, while, in a perfume, eau de toilette or after-shave lotion, this proportion may be substantially less than 50% by weight.

In detergent compositions, in particular household detergents or soaps, the percentage of the compounds prepared according to the invention may range from about 1% to 2%.

The subject compounds may also be present in perfumed shampoos in a percentage by weight of from 0.5% to 2%, or they may be used to perfume any hair-care product.

Accordingly, the lower limit of the percentage of the compounds prepared according to the invention may be that level which causes a perceptible change in the smell of the fragrance, or in the predominating scent of the final product. In certain instances, this minimum percentage may be about 0.01% by weight. Percentages not within the percentage limits indicated above may also be used, while remaining within the scope of the invention.

Among all of the stereoisomeric and acylated stereoisomeric alcohols produced according to the invention, it should be appreciated that alcohol or secondary cyclic acylated alcohol position stereoisomers, and preferably cyclohexanol, are well suited for use in perfumes, one of these stereoisomers having a hydroxyl or ester (preferably acetate) functional group in the axial position, and the other, a hydroxyl or ester (preferably acetate) functional group in the aquatorial position, the configuration being blocked by the presence of a bulky group, preferably a tert-butyl, isobornyl, or isocamphyl group.

A preferred compound is axial 4-tert-butylcyclohexyl acetate, which emits an interesting flowering pine scent.

In order to further illustrate the present invention and the advantages thereof, the following specific examples are given, it being understood that same are intended only as illustrative and in nowise limitative.

In said examples, the following abbreviations are employed:

$$TT = \frac{\text{no. of moles of stereoisomeric alcohols transformed}}{\text{no. of moles of stereoisomeric alcohols introduced}}$$

$$RT_{acylation\ agent} = \frac{\text{no. of moles of ester formed}}{\text{no. of moles of acylation agent transformed}}$$

$$RR_{alcohol} = \frac{\text{no. of moles of ester formed}}{\text{no. of moles of alcohol employed}}$$

$$\text{Enantiomeric excess } ee = \frac{\text{no. of moles of (S)} - \text{no. of moles of (R)}}{\text{no. of moles of (S)} + \text{no. of moles of (R)}}$$

Diastereoisomeric excess $ed$:

$$ed = \frac{\text{no. of moles of equatorial isomer} - \text{no. of moles of axial isomer}}{\text{no. of moles of equatorial isomer} + \text{no. of moles of axial isomer}}$$

Activity = amount of alcohol transformed in g per hour per kg of enzyme.

EXAMPLE 1

Resolution of 1-phenylethanol:
The stereoisomeric mixture indicated below was resolved by acetylation of the (R) enantiomer in accordance with the following reaction mechanism:

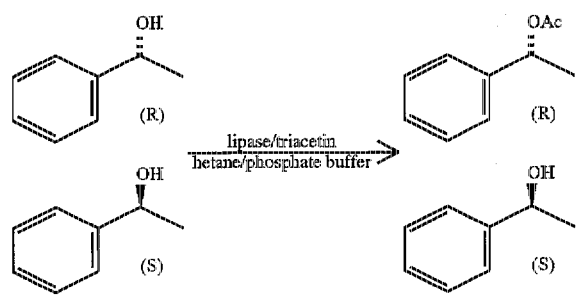

10 mg of lipase PS (from *Pseudomonas fluorescences*), marketed by AMANO, and 0.4 ml of a sodium phosphate buffer having a pH of 7 (100 mmole/l) were introduced into a 4 ml glass tube.

10 mg of 1-phenylethanol (0.082 mmole) dissolved in 0.5 ml of heptane were added.

The aqueous phase was mixed with the organic phase by magnetic stirring.

100 μl (0.5 mmole) of triacetin were added.

After 60 minutes of stirring at room temperature, the transformation ratio was determined by gas phase chromatography (15 m CARBOWAX® column) and the enantiomeric excesses were determined by liquid chiral phase chromatography (CHIRALCEL OJ® column).

The results obtained were as follows:
TT=19%
ee[1-phenylethanol]=24%
ee[1-acetoxy-1-phenylethane]=100%
E>100
Activity=190 g/h.kg enzyme.

EXAMPLE 2

Resolution of hydratropic alcohol:
The stereoisomeric mixture indicated below was resolved by acetylation of the (S) enantiomer in accordance with the following reaction mechanism:

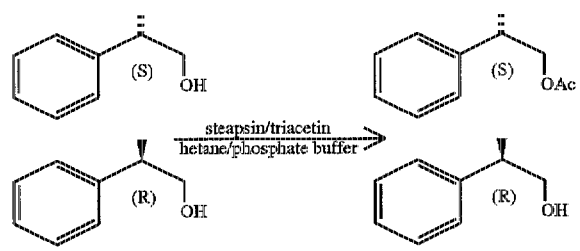

10 mg of steapsin (a lipase from a pig pancreas), marketed by BIOCATALYST, and 0.4 ml of a sodium phosphate buffer having a pH of 7 (100 mmole/l) were introduced into a 4 ml glass tube.

10 mg of 2-phenyl-1-propanol (0.075 mmole) dissolved in 0.5 ml of heptane were added.

The aqueous phase was mixed with the organic phase by magnetic stirring.

100 μl (0.5 mmole) of triacetin were added.

The reaction mixture was maintained at 25° C. for 1 hours, 20 minutes, with stirring.

The reaction mass was analyzed and the transformation ratio was determined by gas phase chromatography (15 m CARBOWAX® column). The enantiomeric excess of the acetate formed was determined by liquid chiral phase chromatography (CHIRALPACK AD).

The results obtained were as follows:
TT=32%
ee[1-acetoxy-2-phenylpropane]=69%
E=7.4
Activity=240 g/h.kg enzyme.

EXAMPLE 3

Resolution of nortricyclanol:
The stereoisomeric mixture indicated below was resolved by acetylation of (−) nortricyclanol in accordance with the following reaction mechanism:

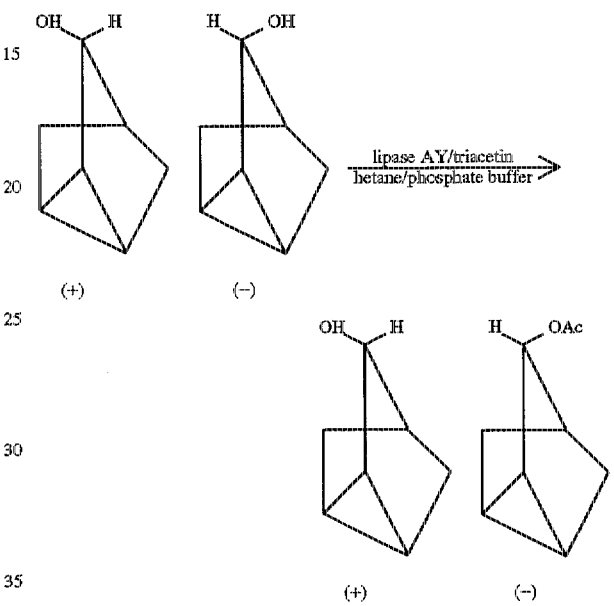

0.5 g of lipase AY (from *Candida cylindracea*) and 40 ml of a sodium phosphate buffer having a pH of 7 (100 mmole/l) were introduced into a 4 ml tube.

2.5 g of nortricyclanol (22.7 mmole) dissolved in 50 ml of heptane were added.

The aqueous phase was mixed with the organic phase by magnetic stirring.

10 g (45 mmole) of triacetin were added.

After 2 hours of stirring at room temperature, the transformation ratio was determined by gas phase chromatography (15 m CARBOWAX® column) and the enantiomeric excess of the acetate was determined by polarimetry after separation of the alcohol and the acetate on a silica column:

ref.$[\alpha]_D$=47.4° in ethyl ether, the reference being defined by Yoshiki Hirose et al [*Chemistry Letters*, pp 1939–1942 (1989)].

The results obtained were as follows:
TT=59%
ee[acetate]=66%
E=17
Activity=1475 g/h.kg enzyme.

EXAMPLE 4

Resolution of menthol:
The stereoisomeric mixture indicated below was resolved by acetylation of (−) menthol in accordance with the following reaction mechanism:

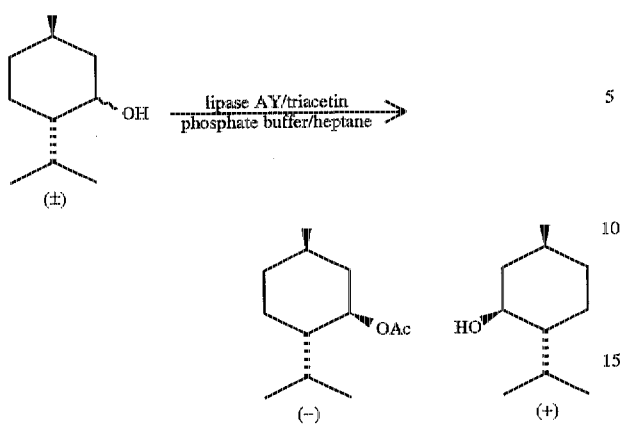

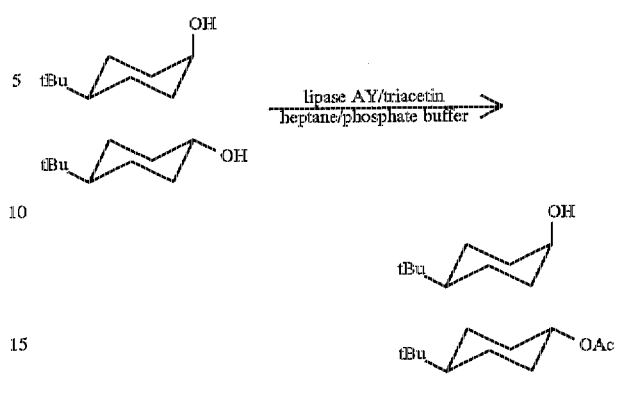

10 mg of lipase AY and 0.4 ml of a sodium phosphate buffer having a pH of 7 (250 mmole/l) were introduced into a 4 ml tube.

10 mg of menthol (0.064 mmole) dissolved in 0.5 ml of heptane were added.

The aqueous phase was mixed with the organic phase by magnetic stirring.

100 μl (0.5 mmole) of triacetin were added.

After 2 hours 30 minutes of stirring at room temperature, the transformation ratio was determined by gas phase chromatography (15 m CARBOWAX® column).

The results obtained were as follows:
TT=47.7%
Activity=191 g/h.kg enzyme.

EXAMPLE 5

Resolution of menthol:

The stereoisomeric mixture was resolved by acetylation of (−) menthol as described in Example 4.

1 g of lipase AY and 40 ml of a sodium phosphate buffer having a pH of 7 (250 mmole/l) were introduced into a 250 ml reactor. 10 g of menthol (64 mmole) dissolved in 50 ml of heptane were added.

The aqueous phase was mixed with the organic phase by magnetic stirring.

10 ml (50 mmole) of triacetin were added.

After 120 hours of stirring at room temperature, 1 g of lipase AY and 10 ml of triacetin were added.

After 170 hours of stirring at room temperature, the reaction was stopped.

Decanting was effected by terminating the stirring and separating the phases.

The aqueous phase was extracted with 50 ml of heptane.

The heptane phases were combined and the solvent was evaporated off.

The alcohol was separated from the acetate on a silica column.

The optical purity of the acetate formed was determined with reference to a commercial (−) menthol standard, by polarimetry using basic hydrolysis (38% KOH+methanol, V/V ratio=1/1).

The results obtained were as follows:
TT=47.5%
ee[acetate]=91%
E=54.

EXAMPLE 6

Resolution of 4-tert-butylcyclohexanol:

The stereoisomeric mixture indicated below was resolved by acetylation of the equatorial isomer in accordance with the following reaction mechanism:

It contained 70% of the equatorial isomer and 30% of the axial isomer.

2 g of lipase AY in 1.25 liter of a sodium phosphate buffer having a pH of 7 (100 mmole/l) were introduced into a 6 liter reactor.

1.25 l of heptane containing 150 g of 4-tert-butylcyclohexanol (961 mmoles) containing 70% of the equatorial isomer and 30% of the axial isomer was added. The reaction was initiated by adding 200 ml of triacetin (975 mmoles).

The reactor was maintained at room temperature and mechanically stirred to microemulsify the system.

The pH of the aqueous phase was regulated at 7 by addition of an aqueous 12N caustic soda solution.

Various additions were made during the reaction:

(a) 0.2 g of lipase after 70 hours; 0.8 g of lipase after 165 hours.

(b) 100 ml of triacetin after 165 hours; 100 ml of triacetin after 189 hours.

After 261 hours, 70.4% of the 4-tert-butylcyclohexanol had been transformed.

The reaction was stopped by decanting and separating the phases.

Conversion of the substrate and the selectivity of the reaction were measured by gas phase chromatography.
TT=70.4%

The aqueous phase was washed with heptane and the organic phases were dried and then evaporated.

180 g of product was recovered.

After separation on a silica column, 130 g of equatorial 4-tert-butylcyclohexyl acetate and 39 g of axial 4-tert-butylcyclohexanol were obtained.

The results obtained were as follows:
ed alcohol=93%
ed acetate=97%.

EXAMPLES 7 TO 10

TESTS (a) TO (d)

Resolution of 4-tert-butylcyclohexanol:

This series of examples illustrated the influence of the nature of the acetylation agent on the transesterification of 4-tert-butylcyclohexanol catalyzed by lipase AY.

The influence of the biphasic heptane/water medium (Examples 7 to 10) with respect to an anhydrous heptane medium (Tests (a) to (d)) was also demonstrated.

EXAMPLES 7 TO 10

10 mg of lipase AY and 0.4 ml of a sodium phosphate buffer having a pH of 7 (100 mmole/l) were introduced into a 4 ml tube.

15.6 mg of 4-tert-butylcyclohexanol (0.1 mmole) dissolved in 0.5 ml of heptane were added.

The aqueous phase was mixed with the organic phase by magnetic stirring.

0.2 mmole of an acylation agent, the nature of which is indicated in Table I, was then added.

After stirring for the period of time indicated in the following Table I, at 25° C., the transformation ratio and the enantiomeric excess were determined by gas phase chromatography.

The conditions and results obtained are reported in Table I.

TESTS a TO d 10 mg of lipase AY, 0.5 ml of heptane and 15.6 mg of 4-tert-butylcyclohexanol (0.1 mmole) were introduced into a 4 ml tube.

The aqueous phase was mixed with the organic phase by magnetic stirring.

0.2 mmole of an acylation agent, the nature of which is indicated in Table I, was then added.

After stirring for the period of time indicated in the following Table I, at 25° C., the transformation ratio and the enantiomeric excess were determined by gas phase chromatography.

The conditions and results obtained are reported in Table I.

TABLE I

| Example/ Test | Acylation agent | Medium | Time (h) | TT alcohol (%) | ed acetate (%) | Activity (g/h · kg of lipase) |
| --- | --- | --- | --- | --- | --- | --- |
| (a) | triacetin | heptane | 1.7 | 39 | 100 | 360 |
| 7 |  | heptane/ water | 0.5 | 37 | 100 | 1,100 |
| (b) | vinyl- acetate | heptane | 2.7 | 15 | 100 | 80 |
| 8 |  | heptane/ water |  | 31 | 91 | 170 |
| (c) | acetic anhydride | heptane | 2.7 | 18 | 100 | 100 |
| 9 |  | heptane/ water |  | 58 | 35 | 325 |
| (d) | ethyl- acetate | heptane | 2.7 | 1 | 100 | 5 |
| 10 |  | heptane/ water |  | 3 | 100 | 17 |

It is apparent from the above Table that the hydroorganic medium was kinetically more favorable. Of the different acylation agents, triacetin was the best acetylation agent, followed by the activated esters.

EXAMPLES 11 TO 14

This series of examples illustrated the influence of the lipase AY content on the acetylation of 4-tert-butylcyclohexanol by triacetin.

x mg of lipase AY and 0.4 ml of a sodium phosphate buffer having a pH of 7 (100 mmole/l) were introduced into a 4 ml tube.

50 mg of 4-tert-butylcyclohexanol (0.32 mmole) dissolved in 0.5 ml of heptane were added.

The aqueous phase was mixed with the organic phase by magnetic stirring.

0.1 ml of triacetin, i.e., 0.5 mmole, was then added.

After a reaction time of 0.5 hours at 25° C., the transformation ratio and the enantiomeric excess were determined by gas phase chromatography.

The conditions and results obtained are reported in Table II:

TABLE II

| Example | Lipase AY (g/l) | TT (%) | Activity (g/h · kg of enzyme) | ed acetate (%) |
| --- | --- | --- | --- | --- |
| 11 | 10 | 19 | 2,000 | 99 |
| 12 | 5 | 12 | 2,500 | 99 |
| 13 | 1 | 2.5 | 2,800 | 99 |
| 14 | 0.5 | 1.7 | 3,300 | 99 |

EXAMPLES 15 TO 19

A competing reaction, hydrolysis of triacetin, was observed during the acetylation reaction of 4-tert-butylcyclohexanol.

This series of examples illustrated the influence of pH on the competition of the hydrolysis and transesterification reactions of triacetin.

A portion of the triacetin was consumed by the hydrolysis reaction and it was found that judicious selection of the pH permitted the hydrolysis to be minimized.

To this end, the yield of triacetin ($RT_{triacetin}$) was determined using the following equation:

$$RT_{triacetin} = \frac{\text{no. of moles of 4-tert-butylcyclohexanol esterified}}{\text{no. of moles of triacetin consumed}}$$

This was determined at different pHs, according to the following operating procedure.

50 mg of lipase AY and 30 ml of a sodium phosphate buffer having a pH of 7 (5 mmole/l) were introduced into a 250 ml reactor.

1 g of 4-tert-butylcyclohexanol (6.4 mmole) dissolved in 50 ml of heptane was added.

The aqueous phase was mixed with the organic phase by magnetic stirring.

20 ml of triacetin (100 mmole) were then added.

During the reaction, the pH was regulated in the examples to a value of 5 to 9 by addition of a 2N aqueous caustic soda solution, which permitted the amount of triacetin which was hydrolyzed to be determined as a function of pH.

The transformation ratio for the 4-tert-butylcyclohexanol was determined by gas phase chromatography.

The results obtained are reported in Table III:

TABLE III

| Example | pH | RT triacetin (%) |
| --- | --- | --- |
| 15 | 5 | 41 |
| 16 | 6 | 36.5 |
| 17 | 7 | 34 |
| 18 | 8 | 26.3 |
| 19 | 9 | 11.9 |

From Table III, it will be seen that the pH must be as low as possible in order to avoid hydrolysis of the triacetin.

EXAMPLES 20 TO 23

The following examples illustrated the influence of the starting substrate concentration on the competition between the hydrolysis reaction and the transesterification reaction.

The operating procedure of Examples 15 to 19 was repeated, the only difference being that the concentration of 4-tert-butylcyclohexanol in the reaction medium was changed.

In these examples, the pH was regulated to 7.0 by addition of a 2N aqueous caustic soda solution.

The results obtained are reported in Table IV:

TABLE IV

| Example | Concentration of 4-tert-butylcyclohexanol (g/l) | RT triacetin (%) |
|---|---|---|
| 20 | 0 | 0 |
| 21 | 1 | 4.1 |
| 22 | 10 | 32.2 |
| 23 | 100 | 36.3 |

From Table IV, it will be seen that it is preferable to employ a high substrate concentration in order to minimize hydrolysis of the triacetin.

EXAMPLES 24 TO 30

These Examples 24 to 30 were carried out at different temperatures according to the operating procedure described below.

20 mg of lipase AY and 0.9 ml of a sodium phosphate buffer having a pH of 7 (100 mmole/l) were introduced into a 4 ml tube.

50 mg of 4-tert-butylcyclohexanol (0.32 mmole) dissolved in 1.0 ml of heptane were added.

The aqueous phase was mixed with the organic phase by magnetic stirring.

On heating, the reaction mass was adjusted to a temperature which differed from example to example, as indicated in Table V.

The reaction was initiated by addition of 100 μl (0.5 mmole) of triacetin.

After 20 minutes of reaction, the reaction mass was analyzed by gas phase chromatography.

The results obtained are reported in Table V:

TABLE V

| Example | Temperature (°C.) | Activity (g/h · kg) |
|---|---|---|
| 24 | 20 | 970 |
| 25 | 30 | 1,240 |
| 26 | 40 | 1,820 |
| 27 | 45 | 2,110 |
| 28 | 50 | 2,400 |
| 29 | 55 | 2,600 |
| 30 | 60 | 2,520 |

The temperature had little effect on the kinetics of the reaction, since the activity only doubled every 25° C.

EXAMPLE 31

The axial 4-tert-butylcyclohexanol prepared in Example 6 was subjected to acetylation via conventional technique, e.g., employing acetyl chloride or acetic anhydride.

Axial 4-tert-butylcyclohexyl acetate having a flowering pine scent was produced.

It should be appreciated that, as compared with a cis/trans mixture of 4-tert-butylcyclohexyl acetate, the scent of the axial isomer-enriched 4-tert-butylcyclohexyl acetate species was more interesting than that of the mixture.

EXAMPLE 32

The equatorial 4-tert-butylcyclohexyl acetate prepared in Example 6 had a green woody scent.

EXAMPLE 33

The hydratropyl acetate (S) prepared in Example 2 had a honeyed jonquil scent.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the resolution of immixture of stereoisomeric alcohols, comprising selectively enzymatically acylating one of the stereoisomers thereof, in the presence of a hydrolase, in a biphasic hydroorganic reaction medium, and thence separating the alcohol stereoisomer from the ester stereoisomer thus formed.

2. The process as defined by claim 1, said immixture of stereoisomeric alcohols comprising a mixture of enantiomers or positional stereoisomers.

3. The process as defined by claim 2, said immixture of stereoisomeric alcohols comprising a mixture of enantiomers of an alcohol having the formula (I):

$$R\text{---}OH \qquad (I)$$

in which R is a hydrocarbon radical having at least 4 carbon atoms comprising a monovalent, substituted or unsubstituted, linear or branched, saturated or unsaturated, acyclic aliphatic radical, or a monocyclic or polycyclic, saturated or unsaturated, carbocyclic or heterocyclic radical, with the proviso that the hydroxy group either may or may not be borne by the asymmetric carbon atom.

4. The process as defined by claim 3, wherein formula (I), R is the residue of a linear or branched, saturated or unsaturated aliphatic chiral alcohol which may be substituted by a cyclic ring member, or of a saturated or unsaturated, monocyclic carbocyclic or heterocyclic chiral alcohol, or of a polycyclic, carbocyclic or heterocyclic chiral alcohol containing at least two saturated and/or unsaturated carbocycles.

5. The process as defined by claim 3, wherein formula (I), R is a linear or branched, saturated or unsaturated, acyclic aliphatic radical.

6. The process as defined by claim 3, wherein formula (I), R is a linear or branched alkyl, alkenyl, alkadienyl or alkynyl radical having from 4 to 40 carbon atoms.

7. The process as defined by claim 3, wherein formula (I), the hydrocarbon chain or backbone of the radical R is interrupted by a heteroatom, or by one of the following groups:

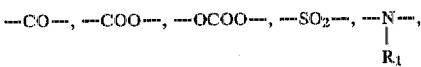

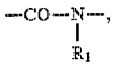

and/or bear one of the substituents ---OH, ---COOR₁, ---CHO, ---NO₂, ---X or CF₃, wherein R₁ is hydrogen or a linear or branched alkyl radical having from 1 to 4 carbon atoms.

8. The process as defined by claim 3, wherein formula (I), R is a linear or branched, saturated or unsaturated, acyclic aliphatic radical optionally substituted by a cyclic substituent bonded thereto by a simple valence bond or via one of the following groups:

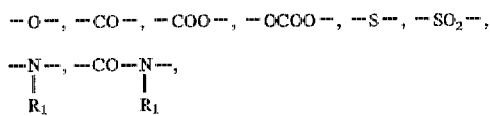

wherein $R_1$ is hydrogen or a linear or branched alkyl radical having from 1 to 4 carbon atoms.

9. The process as defined by claim 3, wherein formula (I), R is a saturated or unsaturated monocyclic carbocyclic or heterocyclic radical having from 3 to 8 ring atoms.

10. The process as defined by claim 3, wherein formula (I), R is polycyclic and carbocyclic.

11. The process as defined by claim 3, wherein formula (I), R is polycyclic and heterocyclic.

12. The process as defined by claim 2, said immixture of stereoisomeric alcohols comprising a mixture of stereoisomers of 2-phenyl-1-propanol, 1-phenylethanol, menthol or nortricyclanol.

13. The process as defined by claim 2, said immixture of stereoisomeric alcohols comprising a mixture of positional stereoisomers.

14. The process as defined by claim 13, said immixture of stereoisomeric alcohols comprising a mixture of the stereoisomers of cyclohexanol.

15. The process as defined by claim 2, said immixture of stereoisomeric alcohols comprising a mixture of stereoisomers of 4-tert-butylcyclohexanol, 4-isobornylcyclohexanol or 4-isocamphylcyclohexanol.

16. The process as defined by claim 1, comprising acylating with an ester of an organic acid, or with an organic acid anhydride.

17. The process as defined by claim 16, comprising acylating with an acylation agent having the formula (II):

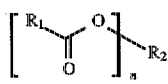

wherein n is a number equal to 1, 2 or 3; $R_1$ is a lower alkyl radical; and if n=1, $R_2$ is a lower alkyl or alkenyl radical or a —CO—$R_3$ radical, in which $R_3$, which may be identical to or different from $R_1$, has the same definition as $R_1$, or if n=2, $R_2$ is a lower alkylene or alkenylene radical, or, if n=3, $R_2$ is a lower triyl alkyl radical.

18. The process as defined by claim 17, said acylation agent comprising an organic acid ester of formula (II), wherein $R_2$ is a methyl or vinyl radical, a halogenomethyl radical, a mono-, di- or trihalogenomethyl radical, a methylsulfate radical, or an ethylsulfate radical, when n=1; a diethylene radical, when n=2; or a propan-1,2,3-triyl radical, when n=3.

19. The process as defined by claim 17, said acylation agent comprising an organic acid anhydride of formula (II), wherein $R_1$ and $R_3$ are identical and are each an alkyl radical having from 1 to 3 carbon atoms.

20. The process as defined by claim 17, said acylation agent comprising triacetin, vinyl acetate or acetic anhydride.

21. The process as defined by claim 1, said hydrolase comprising a lipase, esterase or acylase.

22. The process as defined by claim 21, said hydrolase comprising a carboxylesterase, a triacylglycerol lipase or a triacylglycerol acylase.

23. The process as defined by claim 21, said hydrolase comprising a lipase from an organ of a higher mammal.

24. The process as defined by claim 21, said hydrolase comprising a lipase from the microorganisms *Geotricum candidum*, *Penicillium cyclopium*, *Penicillium rogueforti*, *Candida cylindracea*, *Rhizopus delemar*, *Rhizopus niveus*, *Mucor javanicus*, *Pseudomonas fluorescences*, or *Pseudomonas* species.

25. The process as defined by claim 21, said hydrolase comprising an esterase from pig or horse liver.

26. The process as defined by claim 21, said hydrolase comprising an acylase from a microorganism of the genus Aspergillus.

27. The process as defined by claim 1, the pH of the aqueous phase of said reaction medium being compatible with the activity of the enzyme.

28. The process as defined by claim 1, the organic phase of said reaction medium comprising a water-immiscible organic solvent.

29. The process as defined by claim 28, said organic solvent comprising an aliphatic or aromatic hydrocarbon, an aliphatic or aromatic halogenated hydrocarbon, or an aliphatic, cycloaliphatic or aromatic ether/oxide.

30. The process as defined by claim 28, the ratio by volume between the aqueous phase and the organic phase ranging from 0.1 to 10.

31. The process as defined by claim 28, the amount of enzyme employed ranging from 1% to 10% by weight of the mixture of stereoisomeric alcohols.

* * * * *